US00PP15096P2

(12) United States Plant Patent
Vanderhaegen

(10) Patent No.: US PP15,096 P2
(45) Date of Patent: Aug. 24, 2004

(54) AZALEA PLANT NAMED 'CHRISTINE MAGIC'

(50) Latin Name: *Rhododendron hybrida*
Varietal Denomination: Christine Magic

(75) Inventor: Johan Vanderhaegen, Kruishoutem (BE)

(73) Assignee: Hortibreed NV, Lochristi (BE)

( * ) Notice: Subject to any disclaimer, the term of this patent is extended or adjusted under 35 U.S.C. 154(b) by 0 days.

(21) Appl. No.: 10/716,016

(22) Filed: Nov. 18, 2003

(51) Int. Cl.[7] ..... A01H 5/00
(52) U.S. Cl. ..... Plt./240
(58) Field of Search ..... Plt./240

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Azalea plant named 'Christine Magic', characterized by its vigorous and dense plants that are very freely branching; uniform, upright and outwardly spreading plant habit; very dark green shiny foliage; numerous and showy double red and light pink bi-colored flowers; and long flowering period.

1 Drawing Sheet

Botanical classification: *Rhododendron hybrida* cultivar Christine Magic.

BACKGROUND OF THE INVENTION

The present invention relates to a new and distinct cultivar of Azalea, botanically known as *Rhododendron hybrida,* an evergreen greenhouse-forcing type, and hereinafter referred to by the name 'Christine Magic'.

The new Azalea is a naturally-occurring branch mutation of the *Rhododendron hybrida* cultivar Christine Matton, disclosed in U.S. Plant Pat. No. 11,693. The new Azalea was discovered by the Inventor in a controlled environment in Moerbeke, Belgium in March, 1998. The selection of this plant was based on its unique flower coloration.

Asexual reproduction of the new Azalea by terminal cuttings taken in a controlled environment in Moerbeke, Belgium since November, 1998, has shown that the unique features of this new Azalea are stable and reproduced true to type in successive generations.

BRIEF SUMMARY OF THE INVENTION

The new Azalea has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Christine Magic'. These characteristics in combination distinguish 'Christine Magic' as a new and distinct cultivar:

1. Vigorous and dense plants that are very freely branching.
2. Uniform, upright and outwardly spreading plant habit.
3. Very dark green shiny foliage.
4. Numerous and showy double red and light pink bi-colored flowers.
5. Long flowering period; plants stay in flower for more than three weeks.

Plants of the new Azalea are most similar to plants of the parent, the cultivar Christine Matton. Plants of the new Azalea differ primarily from plants of the cultivar Christine Matton in flower coloration as flowers of 'Christine Matton' are salmon pink in color.

BRIEF DESCRIPTION OF THE PHOTOGRAPHS

The accompanying colored photographs illustrate the overall appearance of the new Azalea, showing the colors as true as it is reasonably possible to obtain in colored reproductions of this type. Colors in the photographs may differ slightly from the color values cited in the detailed botanical description which accurately describe the colors of the new Azalea.

The photograph at the top of the sheet comprises a close-up view of a typical flower of 'Christine Magic'.

The photograph at the bottom of the sheet comprises a side perspective view of a typical flowering plant of 'Christine Magic'.

DETAILED BOTANICAL DESCRIPTION

The aforementioned photographs and following botanical description describe plants grown in a greenhouse and an outdoor nursery in Kruishoutem, Belgium, in 15-cm containers and under conditions which approximate commercial Azalea production conditions. During the production of the plants, day temperatures ranged from 4 to 20° C. and night temperatures ranged from 4 to 15° C. Plants were about 18 months old when the photographs and description were taken. In the following description, color references are made to The Royal Horticultural Society Colour Chart, 2001 Edition, except where general terms of ordinary dictionary significance are used.

Botanical classification: *Rhododendron hybrida* cultivar Christine Magic.

Commercial classification: Evergreen greenhouse-forcing type Azalea.

Parentage: Naturally-occurring branch mutation of the *Rhododendron hybrida* cultivar Christine Matton, disclosed in U.S. Plant Pat. No. 11,693.

Propagation:

*Type.*—By terminal cuttings.

*Time to initiate roots.*—About 30 days at temperatures of 15 to 20° C.

*Time to develop roots.*—About 60 days at temperatures of 4° C.

*Rooting habit.*—Vigorous and finely-branched.

Plant description:

*Plant form and growth habit.*—Perennial, evergreen, upright and outwardly spreading, rounded, uniform plant habit. Vigorous. Numerous flowers per plant. Appropriate for 12 to 16-cm containers.

*Branching habit.*—Freely branching; usually about ten lateral branches develop after removal of terminal apex.

*Plant height, soil level to top of flowers.*—About 20 cm.

*Plant diameter, area of spread.*—About 30 cm.

*Growth rate.*—Moderate.

*Lateral branch description.*—Length: Per year, about 8 to 15 cm of growth. Diameter: About 3 mm. Internode length: About 1 to 2 cm. Texture: Mature, woody; young, green with sparse reddish-brown hairs.

Foliage description:

*Arrangement.*—Alternate; whorled towards lateral branch apices.

*Length.*—About 2 to 5.5 cm.

*Width.*—About 1.5 to 3 cm.

*Shape.*—Elliptic.

*Apex.*—Obtuse.

*Base.*—Acute.

*Margin.*—Entire.

*Texture, upper and lower surfaces.*—Leathery, glabrous.

*Color.*—Developing foliage, upper surface: 137A; shiny. Developing foliage, lower surface: 138A to 138B. Fully developed foliage, upper surface: Close to 139A; shiny. Fully developed foliage, lower surface: 147A to 147B. Venation, upper surface: 144A to 144B. Venation, lower surface: 143C.

*Petiole.*—Length: About 5 mm or less.

Flower description:

*Natural flowering season.*—Spring after sufficient cool period.

*Flower arrangement.*—Flowers arranged singly at terminals. Flowers face upward and outward. Very freely flowering.

*Flower appearance.*—Showy star-shaped double flowers.

*Flower longevity.*—Plants stay in flower for more than three weeks. Flowers persistent.

*Flower bud.*—Length: About 2 to 4 cm. Diameter: About 1 to 1.5 cm. Shape: Narrowly ovoid. Color: 137A to 137B.

*Petals.*—Arrangement: Double. Shape: Spatulate with rounded apex. Margin: Entire with slightly undulating edge which gives a ruffled appearance. Length: Outer whorl of petals: About 5 cm. Inner whorl of petals: About 4 to 5 cm. Width: Outer whorl of petals: About 4 cm. Inner whorl of petals: About 2 to 3 cm. Texture, upper and lower surfaces: Smooth, satiny. Color: When opening, upper and lower surfaces: 43D overlain with 39B; color darkest towards the margins. Fully opened, upper and lower surfaces: 43D overlain with 39B; color darkest towards the margins.

*Sepals.*—Arrangement: Five sepals fused into a star-shaped calyx. Texture, upper and lower surfaces: Pubescent. Shape: Ovate. Margin: Entire. Color: Upper surface, 144C; lower surface, 144C to 144D.

*Peduncles.*—Length: About 1 cm. Diameter: About 3 to 4 mm. Angle: Erect. Strength: Flexible, strong. Color: 144D.

*Reproductive organs.*—Androecium: No stamens observed. Gynoecium: Pistil length: About 1.5 to 2.5 cm. Stigma shape: Oval. Stigma color: 48D. Style length: About 1.2 to 2.2 cm. Style color: Towards the base, 143C; towards the apex, 50D to 50C. Ovary: Whiskered; 141B in color.

*Seed/fruit.*—Seed and fruit production have not been observed.

Disease/pest resistance: Resistance to known pathogens and pests of Azalea has not been observed on plants grown under commercial greenhouse conditions.

Temperature tolerance: Plants of the new Azalea have been observed to tolerate temperatures from 0 to 40° C.

It is claimed:

1. A new and distinct Azalea plant named 'Christine Magic', as illustrated and described.

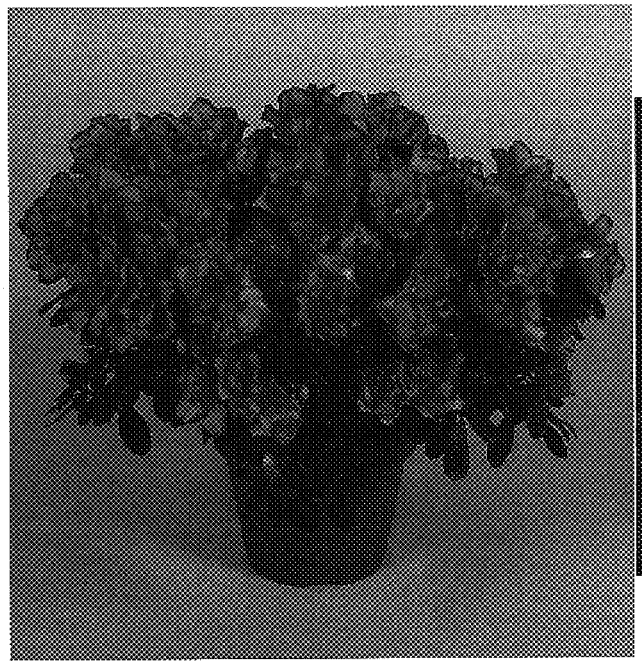
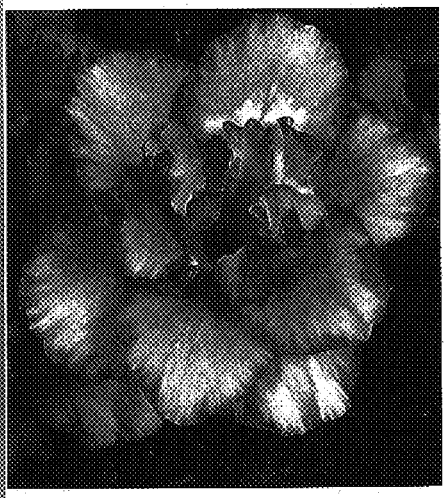

* * * * *